US009362088B2

(12) United States Patent
Sato et al.

(10) Patent No.: US 9,362,088 B2
(45) Date of Patent: Jun. 7, 2016

(54) CHARGED PARTICLE BEAM DEVICE AND SAMPLE PREPARATION METHOD

(71) Applicant: Hitachi High-Technologies Corporation, Minato-ku, Tokyo (JP)

(72) Inventors: Takahiro Sato, Tokyo (JP); Akinari Morikawa, Tokyo (JP); Isamu Sekihara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/434,687

(22) PCT Filed: Oct. 9, 2013

(86) PCT No.: PCT/JP2013/077453
§ 371 (c)(1),
(2) Date: Apr. 9, 2015

(87) PCT Pub. No.: WO2014/061524
PCT Pub. Date: Apr. 24, 2014

(65) Prior Publication Data
US 2015/0255250 A1   Sep. 10, 2015

(30) Foreign Application Priority Data
Oct. 15, 2012   (JP) ................................. 2012-227596

(51) Int. Cl.
*H01J 37/317*   (2006.01)
*G01N 1/28*     (2006.01)
*H01J 37/28*    (2006.01)
*H01J 37/30*    (2006.01)
*H01J 37/31*    (2006.01)

(52) U.S. Cl.
CPC .............. *H01J 37/3178* (2013.01); *G01N 1/28* (2013.01); *G01N 1/286* (2013.01); *H01J 37/28* (2013.01);
(Continued)

(58) Field of Classification Search
CPC .............. H01J 37/3178; H01J 37/3005; H01J 37/3007; H01J 2237/2802; G01N 1/28
See application file for complete search history.

(56) References Cited

U.S. PATENT DOCUMENTS 5,270,552 A     12/1993   Ohnishi et al.
6,452,174 B1 *  9/2002    Hirose ................. H01J 37/304
                                                  250/306

(Continued)

FOREIGN PATENT DOCUMENTS

JP   5-52721 A   3/1993
JP   5-82479 A   4/1993

(Continued)

OTHER PUBLICATIONS

International Search Report (PCT/ISA/210) dated Dec. 10, 2013, with English translation (Five (5) pages).

(Continued)

*Primary Examiner* — Robert Kim
*Assistant Examiner* — Eliza Osenbaugh-Stewar
(74) *Attorney, Agent, or Firm* — Crowell & Moring LLP

(57) ABSTRACT

Provided is a charged particle beam device provided with: a charged particle source; an objective lens for focusing a charged particle beam emitted from the charged particle source onto a sample; a detector for detecting a secondary charged particle emitted from the sample; a probe capable of coming into contact with the sample; a gas nozzle for emitting conductive gas to the sample; and a control unit for controlling the drive of the probe and gas emission from the gas nozzle, wherein before bringing the probe into contact with the sample after applying the charged particle beam to the sample to machine the sample, the control unit emits gas toward a machining position from the gas nozzle and applies the charged particle beam to form a conductive film on a machining portion of the sample, and the charged particle beam device is provided with a contact detection unit for determining that the conductive film formed on the machining portion and the probe have come into contact with each other.

8 Claims, 15 Drawing Sheets

(52) U.S. Cl.
CPC ......... *H01J 37/3005* (2013.01); *H01J 37/3007* (2013.01); *H01J 37/31* (2013.01); *G01N 2001/2873* (2013.01); *H01J 2237/063* (2013.01); *H01J 2237/08* (2013.01); *H01J 2237/208* (2013.01); *H01J 2237/24564* (2013.01); *H01J 2237/2813* (2013.01); *H01J 2237/2817* (2013.01); *H01J 2237/304* (2013.01); *H01J 2237/31745* (2013.01); *H01J 2237/31749* (2013.01)

(56) References Cited

U.S. PATENT DOCUMENTS 6,538,254 B1 * 3/2003 Tomimatsu ......... H01J 37/3056
250/442.11
2004/0129878 A1 * 7/2004 Tomimatsu ......... H01J 37/3056
250/307
2004/0185586 A1 9/2004 Yasutake et al.
2013/0153785 A1 6/2013 Agorio et al.

FOREIGN PATENT DOCUMENTS

| JP | 11-273613 A | 10/1999 |
|---|---|---|
| JP | 2001-235321 A | 8/2001 |
| JP | 2004-245660 A | 9/2004 |
| JP | 2009-224788 A | 10/2009 |
| JP | 2010-507882 A | 3/2010 |

OTHER PUBLICATIONS

International Preliminary Report on Patentability (PCT/IPEA/409) dated Sep. 16, 2014 (Three (3) pages).

* cited by examiner

CHARGED PARTICLE BEAM DEVICE AND SAMPLE PREPARATION METHOD

TECHNICAL FIELD

The present invention relates to a charged particle beam device using a charged particle beam and having automatic preparation function of samples for use in electron microscope observation, and also relates to a sample preparation method.

BACKGROUND ART

Technology relating to charged particle beam devices, especially, focused ion beam (FIB) device, is disclosed in Patent Literature 1. The FIB device utilizes the sputtering phenomenon occurring when irradiating a focused ion beam to a sample, and is able to perform microfabrication of the sample. Recently, the technology relating to combinations of FIB device and SEM or STEM device is disclosed in Patent Literature 2. Such FIB-SEM device and FIB-STEM device are arranged so that an FIB irradiation axis and an electron beam irradiation axis are disposed at acute angles, at an intersection of which a sample is placed. Accordingly, they are characterized by having an ability to achieve direct SEM observation of an FIB-processed cross-section.

According to Patent Literature 3, JP-A-05-052721, a micro-sampling method is disclosed therein, which extracts a desired region from a sample within FIB processing/fabrication apparatus and is able to manufacture a thin-film sample for use in transmission electron microscope (TEM) observation or scanning transmission electron microscope (STEM) observation. This technique includes process steps consisting essentially of conductive film formation, peripheral machining/processing, bottom cutting, mechanical probe fastening, support section cutting, micro-sample extraction, fastening it to sample table, mechanical probe cutting, and thin-film fabrication. Traditionally, all of these processes have been manually operated by a user(s).

CITATION LIST

Patent Literature

PATENT LITERATURE 1: JP-A-5-82479
PATENT LITERATURE 2: JP-A-11-273613
PATENT LITERATURE 3: JP-A-05-052721

SUMMARY OF INVENTION

Technical Problem

FIB fabrication methodology is a technique for irradiating a focused ion beam onto a sample and for performing microfabrication using the sputtering phenomenon. In FIB fabrication of dielectric materials such as ceramics, polymer or the like, electrification tends to readily occur due to the accumulation of electrical charges as a result of ion irradiation. Upon occurrence of such electrification, abnormal light-dark contrast can take place within a field of view of observation in some cases; in other cases, drifting of the observation viewfield occurs. This becomes the cause of image quality degradation and/or fabrication position accuracy deterioration. Consequently, as the preceding processing of FIB fabrication, a process is done of coating an entire surface of the sample with a conductive material for the purpose of preventing electrification.

This preprocessing is also useful not only for the electrification prevention but also for detection of contact of a sample and a mechanical probe for use in the microsampling method. More specifically, electrical conduction is secured between the mechanical probe and sample, thereby making the contact detection operable.

However, there is a problem which follows: part of the sputter material which were created in the process of performing peripheral machining/fabrication and cutting bottom portions behaves to reattach to a machined sample surface, side surface, bottom cut plane and the like, resulting in the electrical conductivity becoming no longer secured. Another problem is that the conductive material is undesirably sputtered by the beam flare of FIB, making it impossible to secure electrical conduction. Hence, the automatic extraction suffers from a problem that the applicability is lost because the contact detection does not operate perfectly. In prior known manual manipulation, it was a must for the user(s) to perform contact check from delicate contrast changes or position changes when the mechanical probe and sample are contacted together. This has been done while at least partly relying upon the user's experience.

A very small or "micro" sample extracted is fastened to an electrically conductive sample table. However, since dielectric material has no conductivity, there has been a problem that the contact detection does not operate when the micro-sample is in contact with the sample table. Thus, with the automatic fabrication, the contact detection does not operate perfectly; so, it suffers from a problem as to the inability to fasten the micro-sample to sample table. With traditional manual manipulation, the user was compelled to ascertain contact with the sample table from contrast changes and position changes in a similar way to the work at the time of extracting the micro-sample. This has relied upon the user's experience at least partly.

An object of the present invention relates to solving the contact detection problem relying upon the user's experience in the prior art and providing a sample preparation method using the above-stated automatic processing.

Solution to Problem

In view of the object stated above, this invention has the following constituent feature: a charged particle beam device comprising a charged particle source, an objective lens for focusing a charged particle beam emitted from said charged particle source onto a sample, a detector for detecting secondary charged particles to be emitted from said sample, a probe capable of coming into contact with said sample, a gas nozzle for emitting a conductive gas to said sample, and a control unit for controlling driving of said probe and gas emission from said gas nozzle, wherein after having processed said sample by irradiating the charged particle beam to said sample, said control unit forms a conductive film at a processing part of said sample by emitting the gas from said gas nozzle toward a processing position and irradiating said charged particle beam prior to causing said probe to come into contact with the sample, and that a contact detection unit is provided for judging that said conductive film formed at the processing part and said probe are contacted together.

Regarding other objects and configurations, objects and configurations plus effects other than those stated supra will be apparent from the following description of preferred embodiments of the invention.

Advantageous Effects of Invention

According to this invention, it becomes possible to solve the problem of contact detection relying on the user's experience in the prior art and also to provide a sample preparation method using the above-stated automatic processing.

Other objects, features and advantages of this invention will be apparent from the following description of embodiments of the invention, as illustrated in the accompanying drawings.

DESCRIPTION OF EMBODIMENTS

Figure 1:
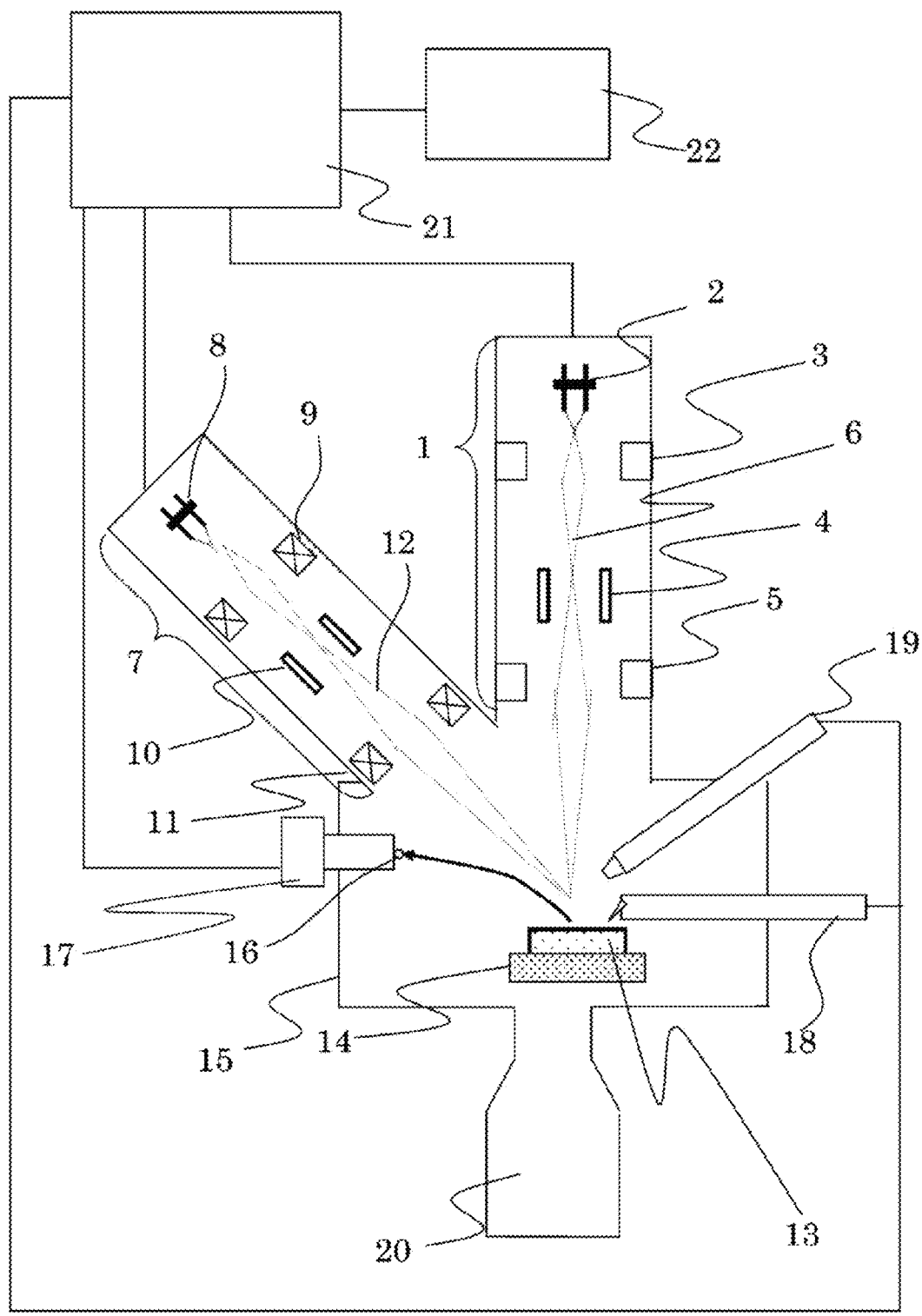
FIG. 1 is a diagram schematically showing a configuration of a charged particle beam device in accordance with one embodiment of this invention.

FIG. 1 is a diagram schematically showing a configuration of a charged particle beam device capable of performing SEM observation within the same chamber as microfabrication based on FIB machining An ion beam irradiation system 1 is constituted from an ion source 2, focusing lens 3, deflector 4 and objective lens 5, and has the function of forming an ion beam 6 and focusing/scanning it on a sample surface. An electron beam irradiation system 7 is configured from an electron source 8, focusing lens 9, deflector 10 and objective lens 11 and has the function of forming an electron beam 12 and focusing/scanning it on the sample surface. An original sample 13 is fastened onto a sample stage 14. Provided in a chamber 15 are the ion beam irradiation system 1, electron beam irradiation system 7, sample stage 14, a secondary charged particle detector 17 which detects secondary charged particles 16 that were generated due to irradiation of the ion beam 6 and electron beam 12, a mechanical probe 18 capable of extracting a very small or "micro" sample, a deposition nozzle 19 capable of performing film formation by gas blowout, and a vacuum pump 20. These are controlled by a control unit 21. An optical system's setup window and secondary charged particle beam image are displayed on CRT 22. On the sample stage 14, a sample table is installable, which is for fastening original sample 13 and a micro-sample which was extracted using mechanical probe 18. The ion beam irradiation system 1 and electron beam irradiation system 7 are able to scan the same portion on original sample 13 and micro-sample.

Figure 2:
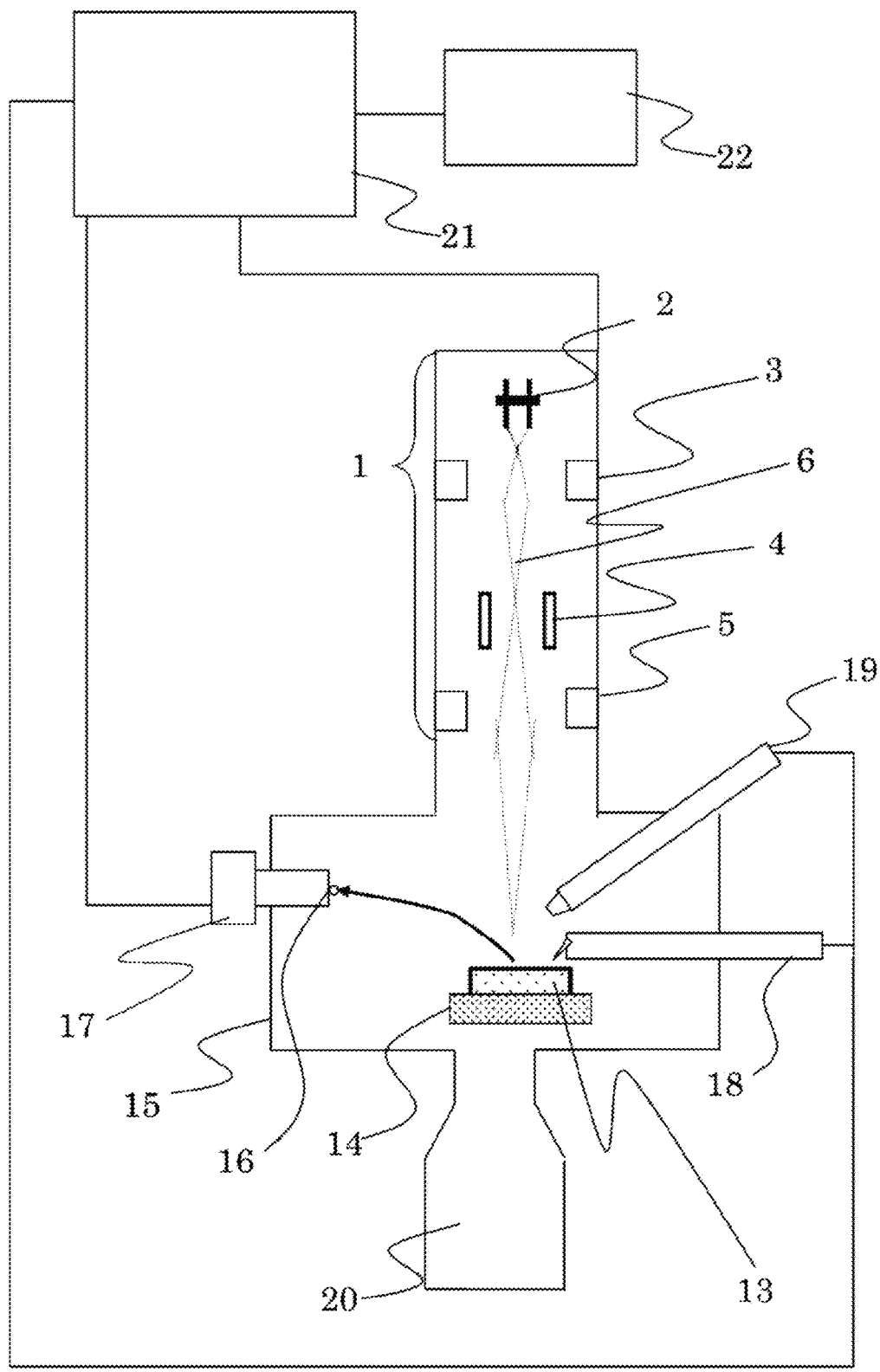
FIG. 2 is a diagram schematically showing a configuration of a charged particle beam device in accordance with one embodiment of this invention.
Figure 3A:
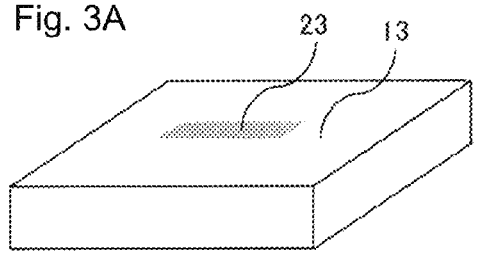
FIGS. 3A-3I are diagrams schematically showing a commonly-used procedure of standard microsampling method.
Figure 3F:
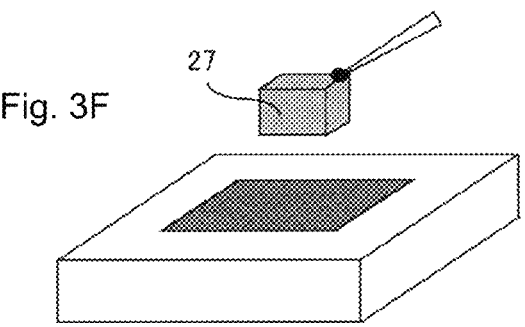
Figure 3B:
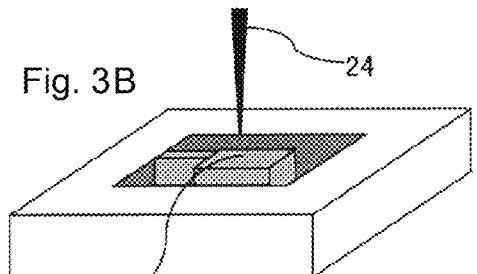
Figure 3G:
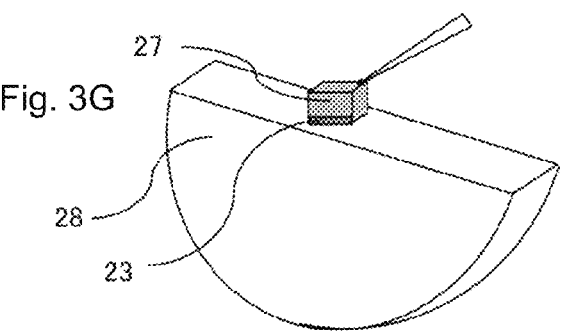
Figure 3C:
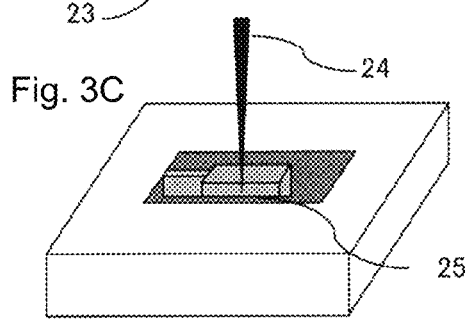
Figure 3H:
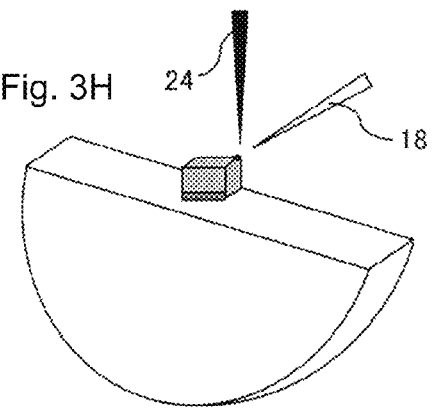
Figure 3D:
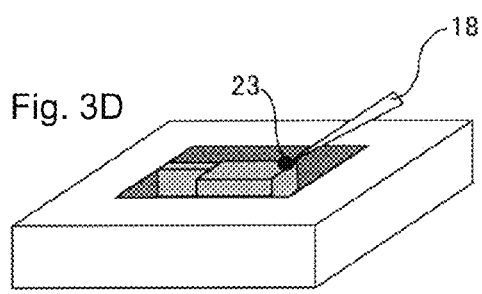
Figure 3I:
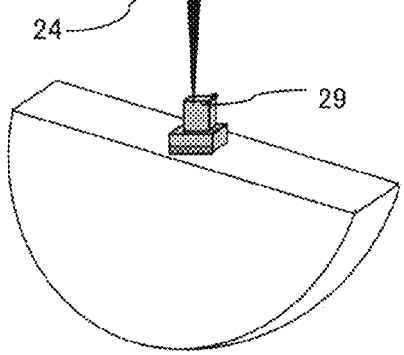
Figure 3E:
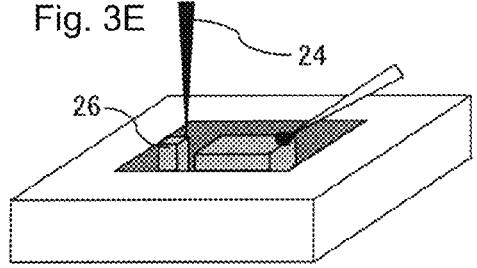

FIG. 2 is a schematic diagram showing a configuration of a charged particle beam device capable of performing FIB processing-based microfabrication. An ion beam irradiation system 1 is constituted from an ion source 2, focusing lens 3, deflector 4 and objective lens 5, and has the function of forming an ion beam 6 and focusing/scanning it on a sample surface. An original sample 13 is fixed onto sample stage 14. Provided in chamber 15 are ion beam irradiation system 1, sample stage 14, secondary charged particle detector 17 for detecting secondary charged particles 16 produced due to irradiation of ion beam 6, mechanical probe 18 capable of extracting a micro-sample, deposition nozzle 19 capable of performing film formation by gas blowout, and vacuum pump 20. These are controlled by control unit 21. The optical system's setup window and secondary charged particle beam image are displayed on CRT 22. On sample stage 14, a sample table is installable, which is for fastening original sample 13 a micro-sample extracted using mechanical probe 18. The ion beam irradiation system is able to scan on original sample 13 and micro-sample.

FIG. 3 shows a procedure of commonly-used microsampling method. Original sample 13 is inserted into the charged particle beam device; then, a conductive film 23 is fabricated on the surface of original sample 13 by the deposition function (see part (a) of FIG. 3). Next, by FIB 24, peripheral machining/fabrication is performed while letting conductive film 23 remain ((b) of FIG. 3). The sample is tilted, and its bottom portion 25 is cut by FIB 24 ((c) of FIG. 3). Let the sample tilt turn back. The mechanical probe 18 is forced to come into contact with the sample surface. The deposition function is used to form conductive film 23; then, the mechanical probe and sample are fastened together ((d) of FIG. 3). A supporting section 26 is cut away by FIB 24 ((e) of FIG. 3). A micro-sample 27 is extracted ((f) of FIG. 3). The micro-sample 27 extracted is brought into contact with sample table 28. The deposition function is used to form conductive film 23; then, fasten micro-sample 27 and sample table 28 together ((g) of FIG. 3). Mechanical probe 18 is cut by FIB 24 ((h) of FIG. 3). FIB 24 is used to apply microfabrication to the micro-sample, thereby making a thin-film sample 29 ((i) of FIG. 3). Currently, those process steps of from the conductive film formation ((a) of FIG. 3) up to the sample extraction ((f) of FIG. 3) and the process of thin-film microfabrication ((i) of FIG. 3) are automated.

Figure 4:
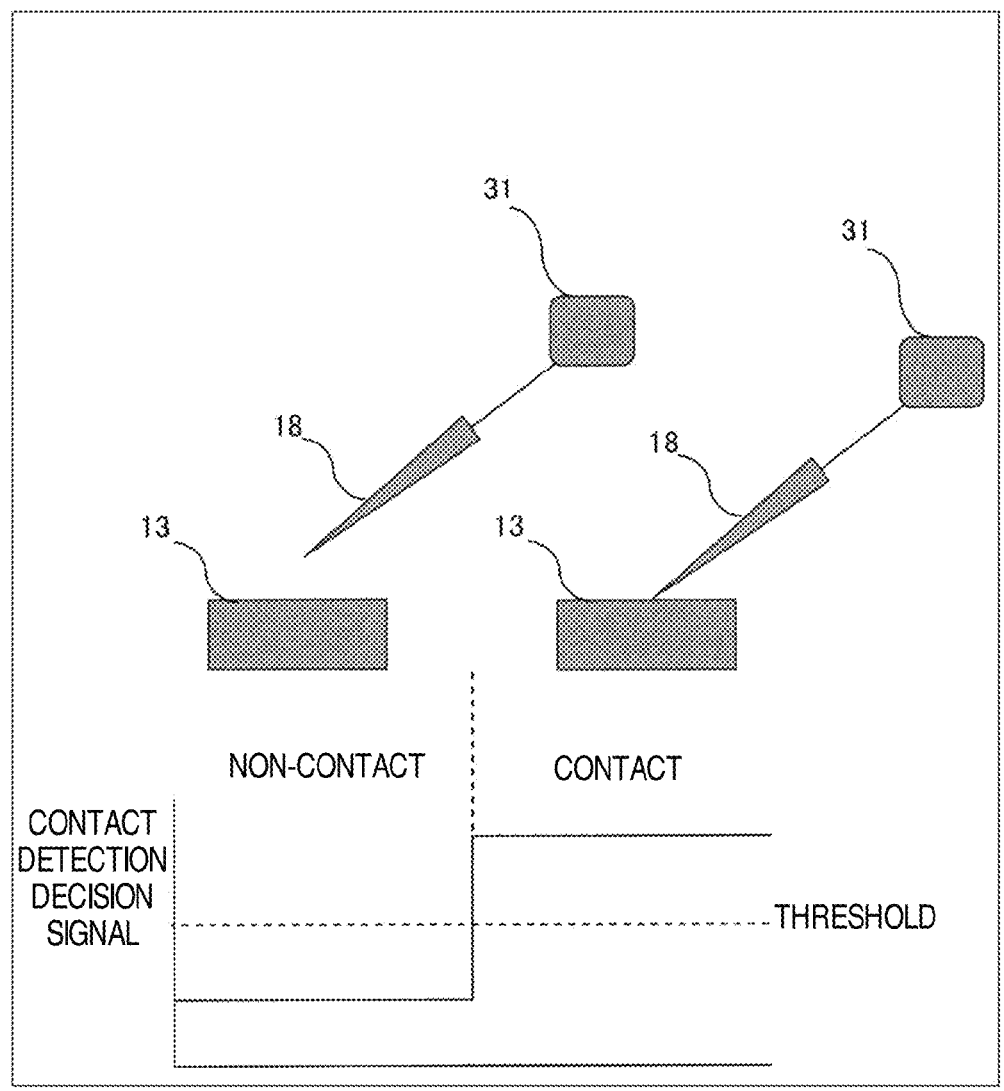
FIG. 4 is a diagram schematically showing a method for detecting contact with a sample using mechanical probe.

FIG. 4 shows a method for detecting contact with a sample by using mechanical probe. Mechanical probe 18 is in contact with a contact detection judging unit 31. This contact detection judging unit 31 is able to read a contact detection decision signal between sample 13 and mechanical probe 18. When the contact detection decision signal is lower than or equal to a prespecified threshold, a judgment of non-contact is made; when greater than the threshold, a judgment of contact is made.

Figure 5A:
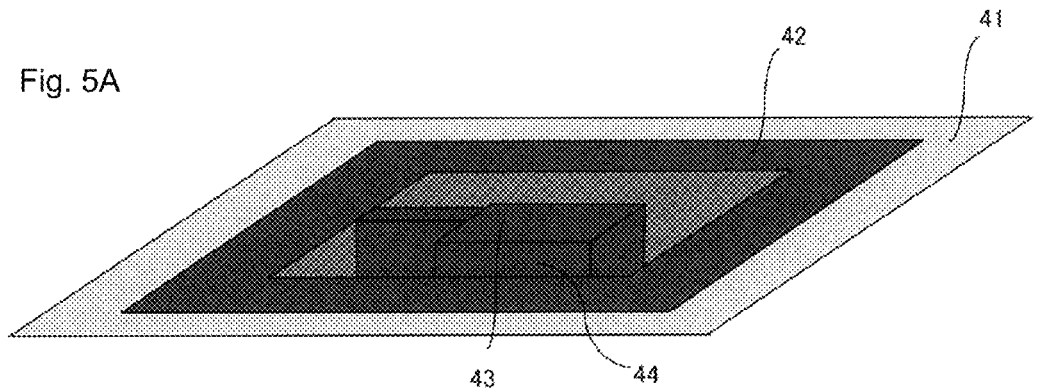
FIGS. 5A-5C are diagrams schematically showing one embodiment of a conductive film formation to sample surface in accordance with this invention.
Figure 5B:
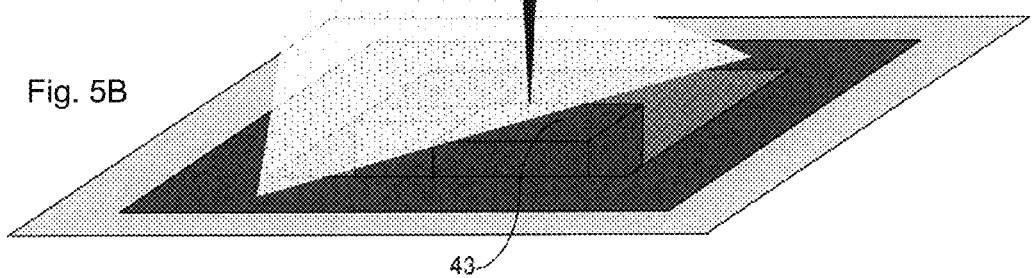
Figure 5C:
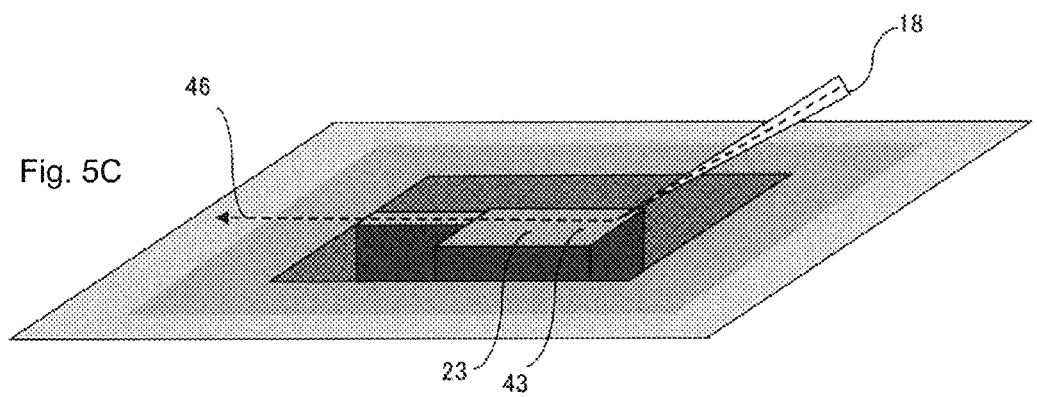
Figure 6A:
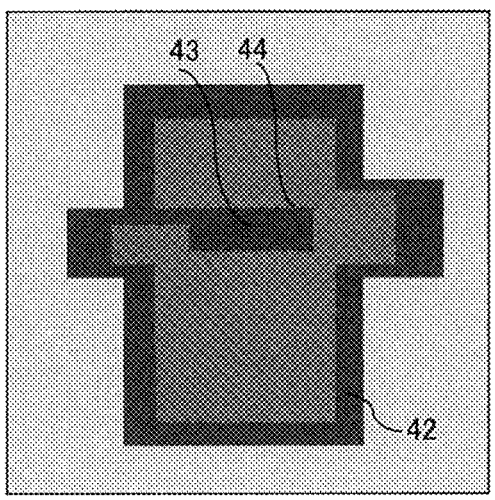
FIGS. 6A-6E are diagrams schematically showing one embodiment of a conductive film formation to sample surface in accordance with this invention.
Figure 6B:
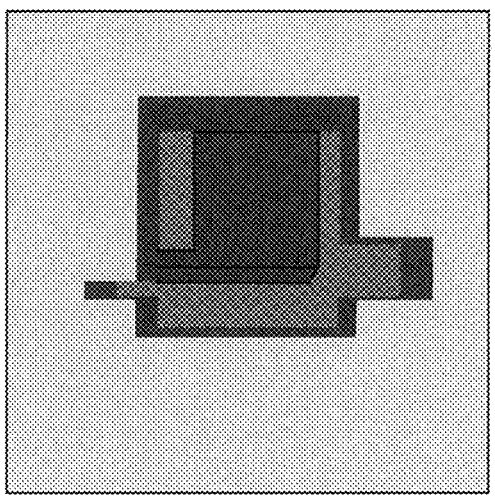
Figure 6C:
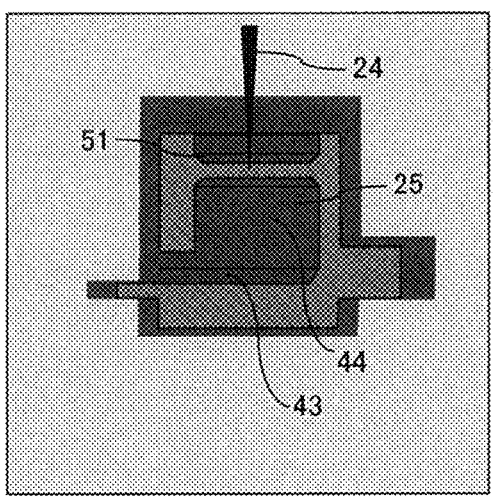
Figure 6D:
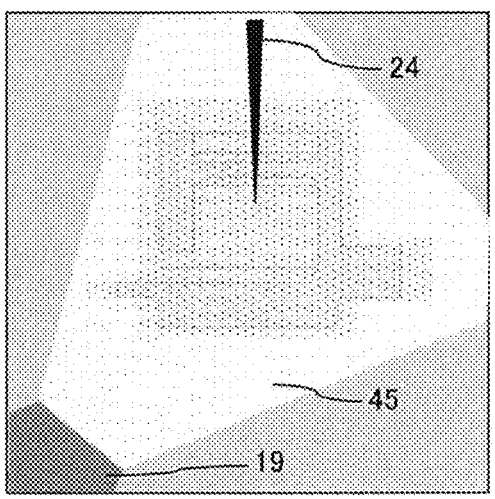
Figure 6E:
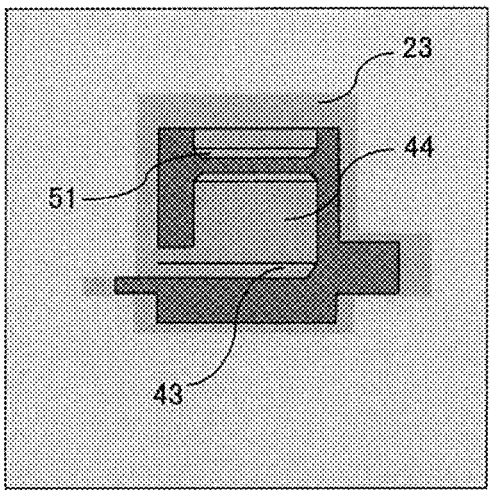

FIG. 5 and FIG. 6 are embodiments of the conductive film formation to sample surface in accordance with this invention. These embodiments are implementable by any one of FIB device, FIB-SEM device and FIB-STEM device. As an example which becomes unable to secure electrical conduction between the mechanical probe and sample surface, there is reattachment of FIB machining-generated sputter material to the sample surface. First of all, prior to inserting the original sample into charged particle beam device, the sample surface is entirely coated with conductive material. This is in order to prevent electrification and render the mechanical-probe/sample contact detection function operative. After the coating, a sample is inserted into the charged particle beam device. Firstly, its positioning function is used to form a conductive film on the surface of a target region being observed and also to perform peripheral machining/fabrication and bottom cutting. These works are implementable without receiving the influence of electrification because the conductive material 41 has already been coated ((a) of FIG. 5). However, sputter material 42 which was generated in the peripheral machining and bottom cutting events reattaches to a top surface 43 and side surface 44. As the processed part is electrically isolated, electrical conduction between mechanical probe and sample is no longer securable, posing a problem that the contact detection becomes inoperable. To avoid this, a conductive film is formed on the surface 43 by using the deposition function ((b) of FIG. 5). Part (b) of FIG. 5 shows a way of forming a conductive film while spouting a gas 45 from deposition nozzle 19 and simultaneously irradiating FIB 24. With this processing, conductive film 23 is formed on surface 43, and an electrical conduction path 46 is secured between mechanical probe 18 and surface 43; thus, the contact detection becomes operable properly ((c) of FIG. 5).

FIG. 6 is an embodiment of the conductive film formation on sample surface in accordance with this invention. The observation direction of each figure is set to the incoming direction of FIB. In a similar way to FIG. 5, it is assumed that sputter material 42 reattached to top surface 43 and side surface 44 ((a) of FIG. 6). The sample inclines ((b) of FIG. 6). Subsequently, in figures of from part (b) of FIG. 6 to (e) of FIG. 6, the scale is shrunk in a longitudinal direction because observation is being done in the state that the sample is slanted or tilted. By FIB 24, bottom portion 25 is cut ((c) of FIG. 6). Next, deposition is applied to the processed portion's top surface 43, side surface 44 and bottom cut plane 51.

Part (d) of FIG. 6 shows a way of forming a conductive film while spouting gas 45 from deposition nozzle 19 and irradiating FIB 24. In order to apply deposition to the bottom cut plane more reliably, the deposition may be performed in the state with a further inclination from the bottom cut angle. With this processing, conductive film 23 is formed on top surface 43, side surface 44 and bottom cut plane 51, and it is possible to secure an electrical conduction path between the mechanical probe and sample surface; thus, the contact detection becomes operating properly ((e) of FIG. 6).

Figure 7A:
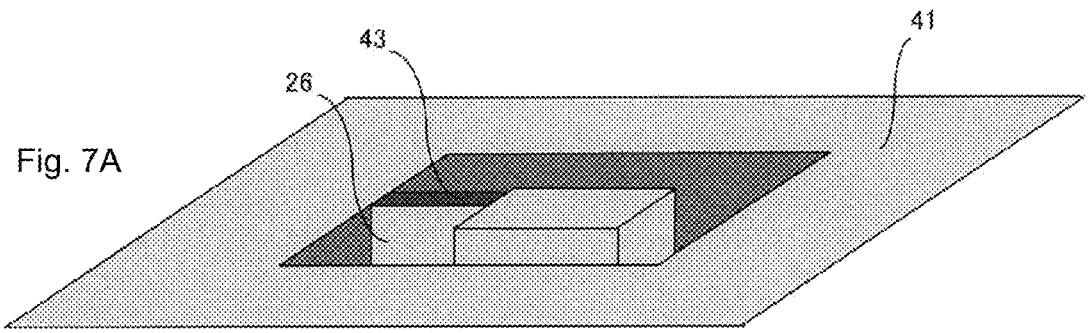
FIGS. 7A-7C are diagrams schematically showing one embodiment of a conductive film formation to sample surface in accordance with this invention.
Figure 7B:
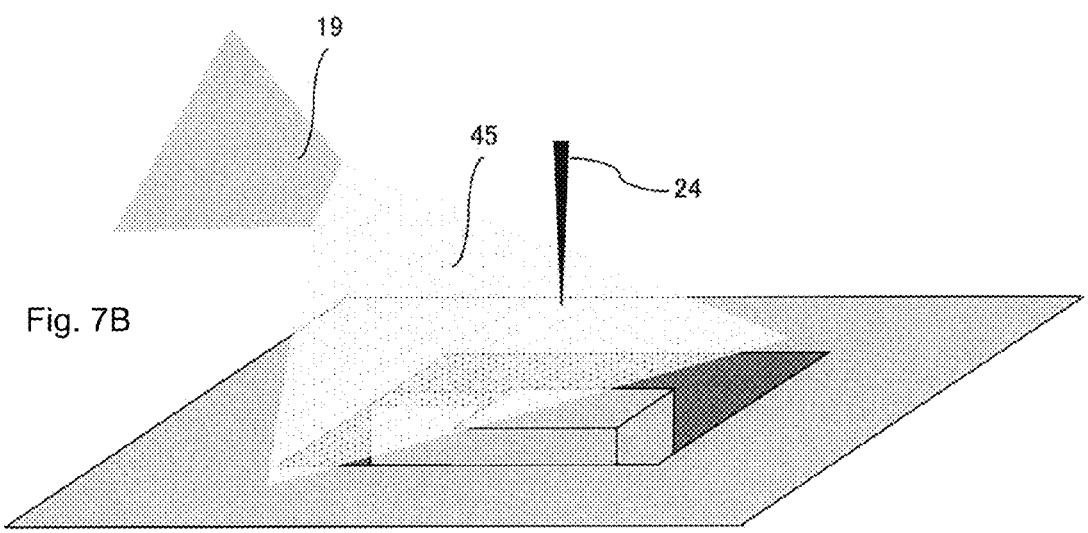
Figure 7C:
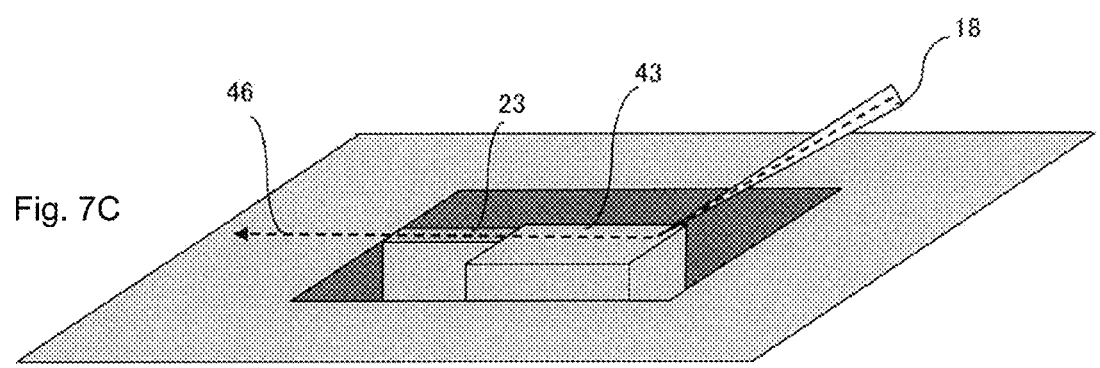
Figure 8A:
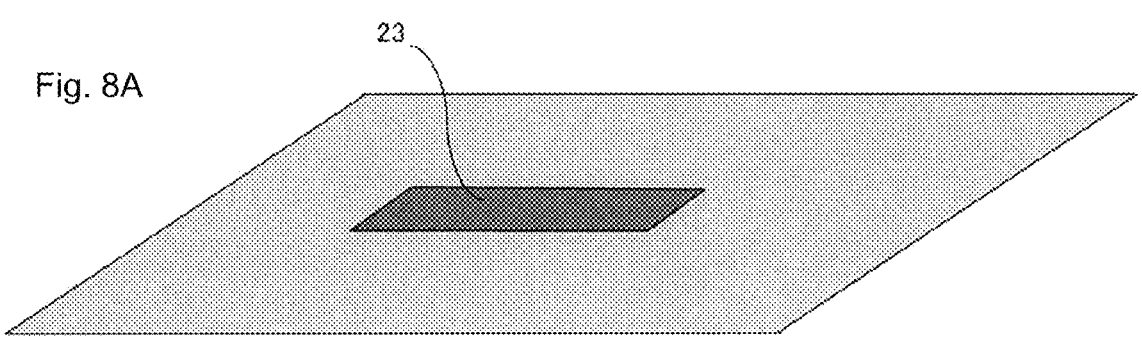
FIGS. 8A and 8B are diagrams schematically showing one embodiment of a conductive film formation to sample surface in accordance with this invention.
Figure 8B:
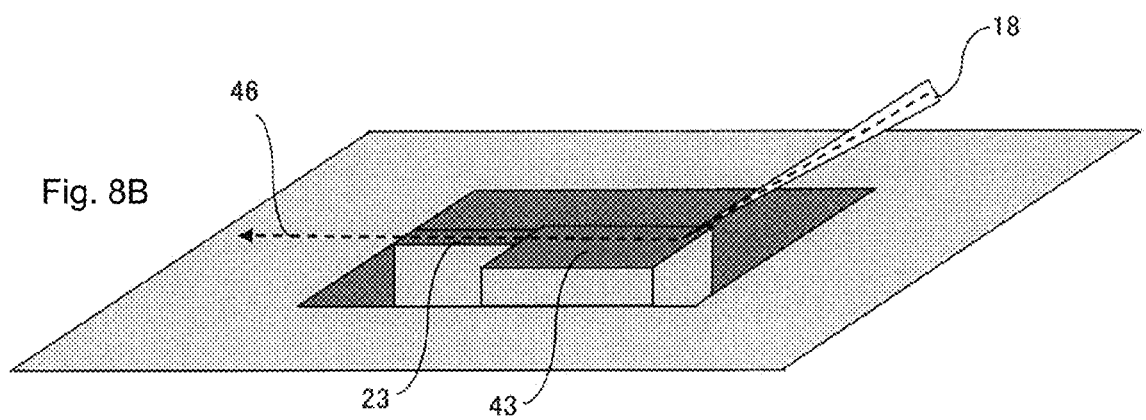
Figure 9A:
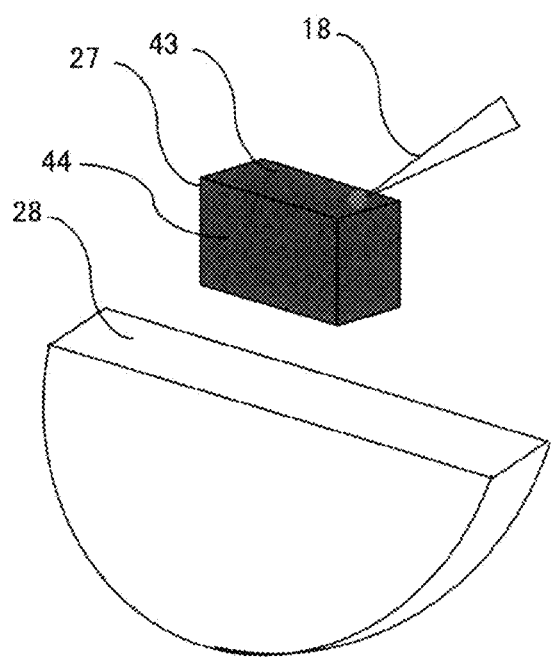
FIGS. 9A-9D are diagrams schematically showing one embodiment of conductive film formation to top and side surfaces of a micro-sample in the case of fastening to a sample table the bottom portion of the extracted micro-sample in accordance with this invention.
Figure 9B:
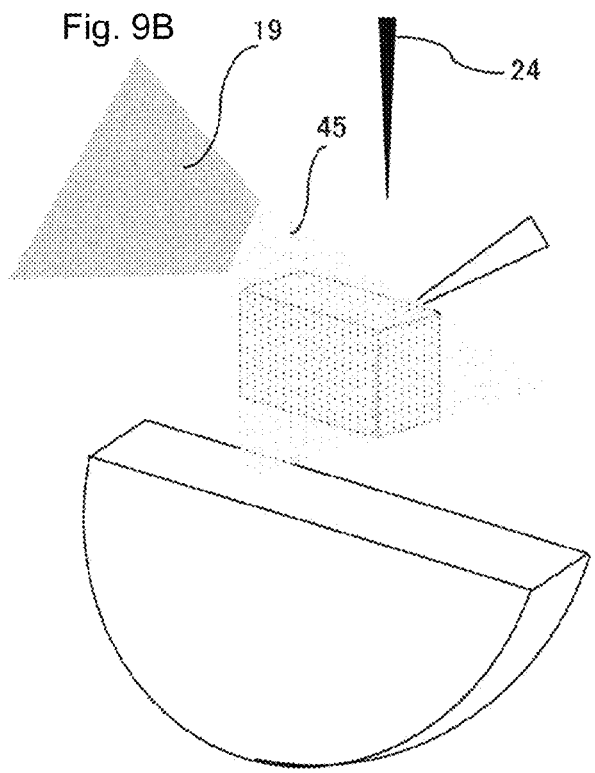
Figure 9C:
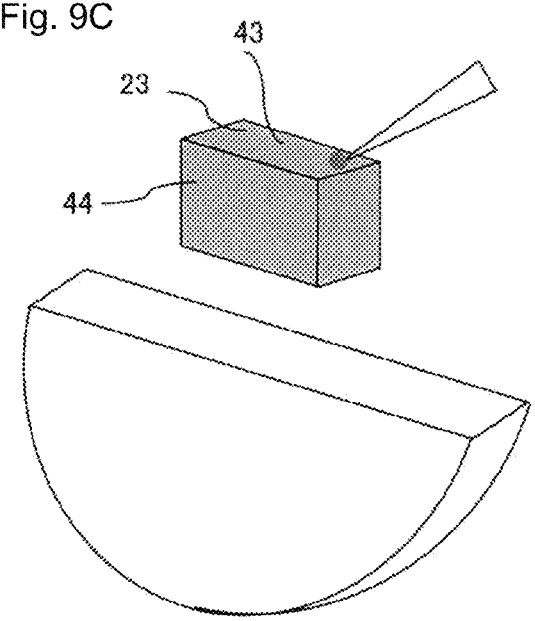
Figure 9D:
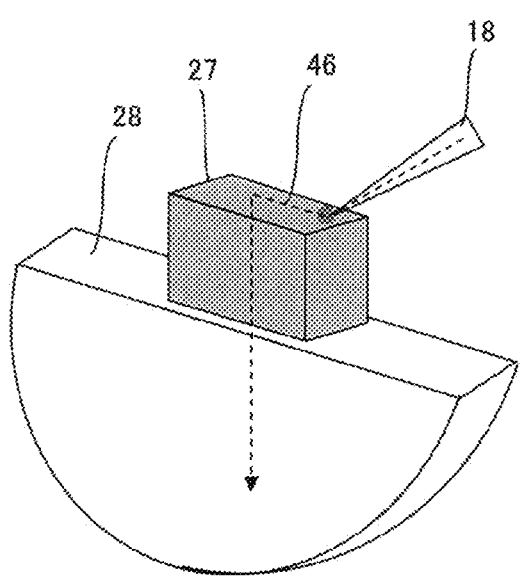
Figure 10A:
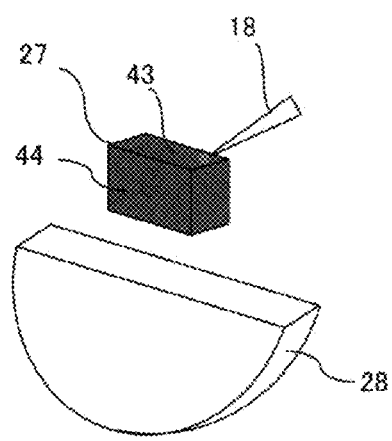
FIGS. 10A-10G are diagrams schematically showing one embodiment of conductive film formation to top and side surfaces of a micro-sample in the case of fastening to a sample table the bottom portion of the extracted micro-sample in accordance with this invention.
Figure 10B:
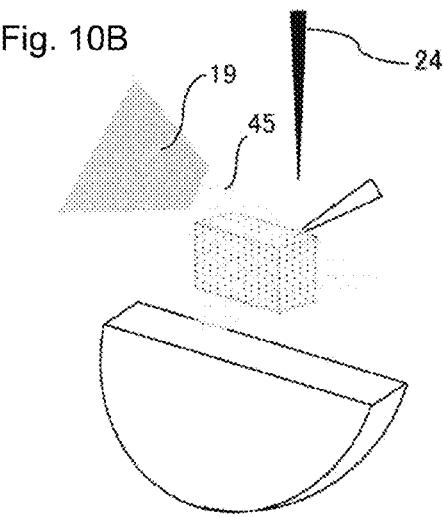
Figure 10C:
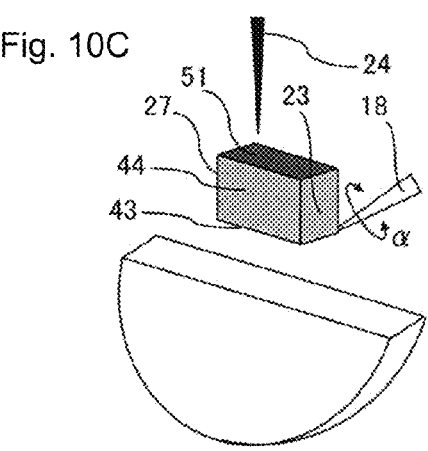
Figure 10D:
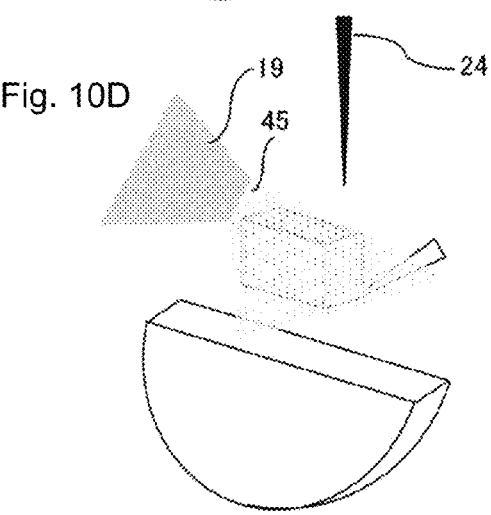
Figure 10E:
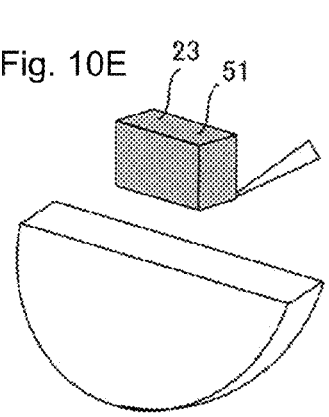
Figure 10F:
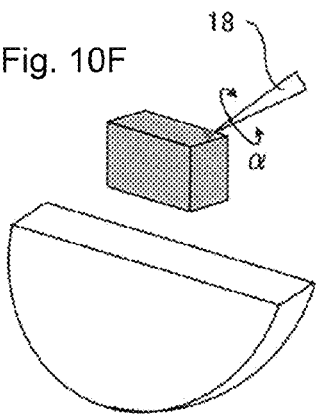
Figure 10G:
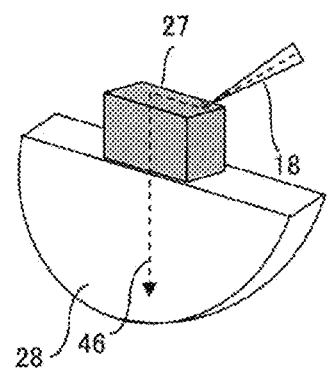
Figure 11A:
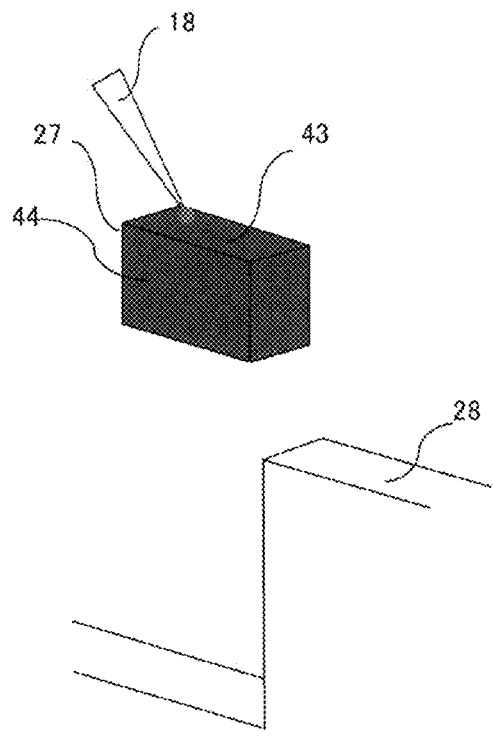
FIGS. 11A-11D are diagrams schematically showing one embodiment of conductive film formation to top and side surfaces and bottom cut plane of a micro-sample in the case of fastening to the sample table the bottom portion of the extracted micro-sample in accordance with this invention.
Figure 11B:
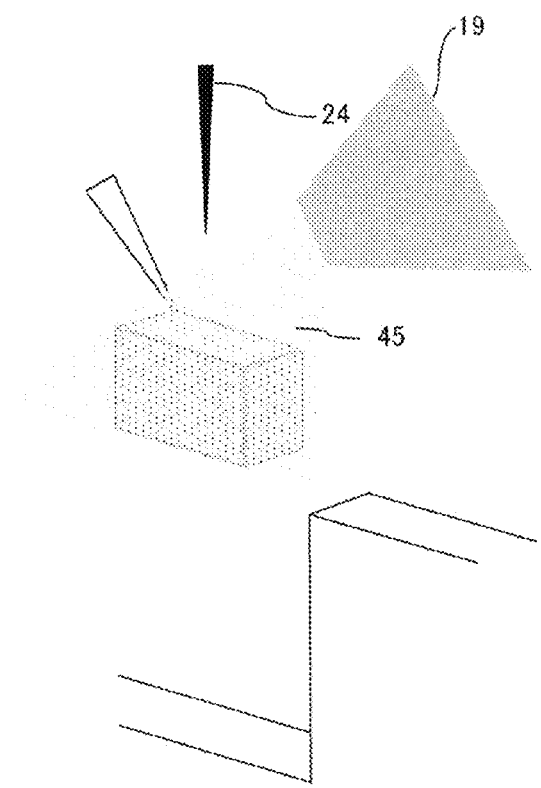
Figure 11C:
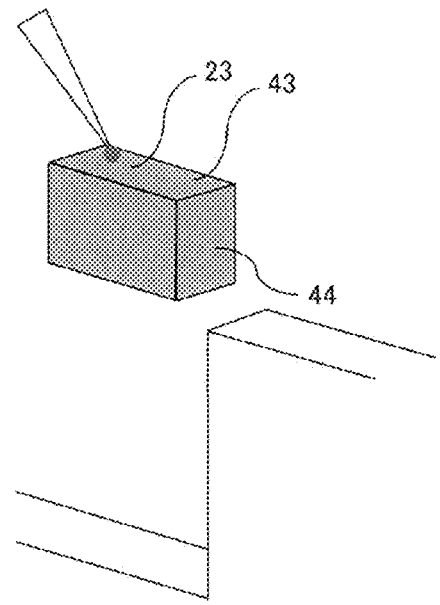
Figure 11D:
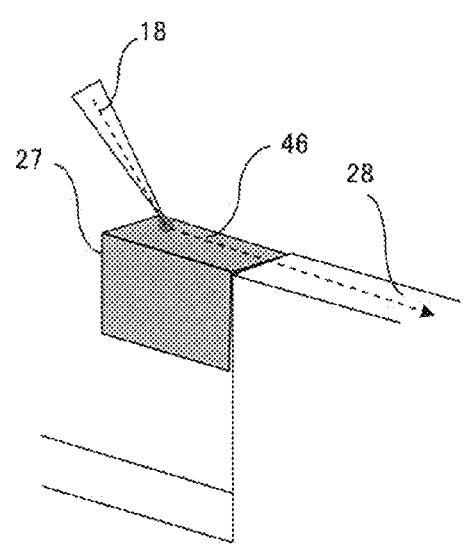

FIG. 7 and FIG. 8 show embodiments of the conductive film formation on sample surface in accordance with this invention. These embodiments are implementable by any one of FIB device, FIB-SEM device and FIB-STEM device. As an example incapable of securing electrical conduction between the mechanical probe and sample surface, there is disappearance of the conductive material overlying the supporting section. Generically, the beam intensity of FIB accedes to Gauss distribution: a central part is the strongest; peripheral portions become weaker. The surface of peripheral portion of processed region is slightly sputtered undesirably due to the influence of beam intensity-weakened part (beam flare). Especially, at the supporting section, this influence tends to occur dominantly because of the shortness of the length of a direction orthogonal to the longitudinal direction. In addition, when the processing time becomes longer, the sputtering of on-surface conductive material becomes prominent. For these reasons, it is impossible to secure the electrical conduction between mechanical probe and sample surface, posing a problem that the contact detection becomes disabled. Consequently, deposition is applied to the surface 43 of supporting section 26 with the conductive material 41 having disappeared after peripheral processing ((a) of FIG. 7). Part (b) of FIG. 7 shows a way of forming a conductive film while spouting gas 45 from deposition nozzle 19 and performing scanning by FIB 24. Owing to this processing, conductive film 23 is formed, and it becomes possible to secure electrical conduction path 46 between mechanical probe 18 and surface 43 ((c) of FIG. 7). Additionally, in the deposition upon startup of the microsampling, the conductive film 23 may be formed above the supporting section ((a) of FIG. 8). Preferably, the thickness of such conductive film at this time is adjusted to become little thicker to ensure that it does no disappear due to the beam flare. By this processing, the conductive film 23 overlying the supporting section does no longer disappear even when after having performed the peripheral processing; thus, it becomes possible to secure the electrical conduction path 46 between mechanical probe 18 and surface 43 ((b) of FIG. 8).

The micro-sample with the mechanical probe fastened thereto is extracted after having cut the supporting section and is then fixed onto the sample table. Detection of contact with the mechanical probe, the extracted micro-sample and the sample table is performed by electrical conduction detection therebetween. However, in some cases, e.g., in the case of the sample being made of dielectric material and in the case of sputter material being attached thereto, electrical conduction is not securable, posing a problem that the contact detection does not operate properly. FIG. 9, FIG. 10 and FIG. 11 show embodiments of the conductive film formation to sample in accordance with this invention. These embodiments are implementable by any one of FIB device, FIB-SEM device and FIB-STEM device. FIG. 9 shows an embodiment of the conductive film formation to top and side surfaces of a micro-sample in the case of fastening the micro-sample's bottom portion to the sample table. Part (a) of FIG. 9 is a diagram schematically showing a state prior to causing a micro-sample 27 which was extracted by mechanical probe 18 to come into contact with the top face of sample table 28. Next, deposition is applied to the top surface 43 and side surface 44 of micro-sample 27. Part (b) of FIG. 9 shows a way of forming a conductive film while spouting gas 45 from deposition nozzle 19 and irradiating FIB 24. By this processing, conductive film 23 is formed on surface 43 and side face 44 ((c) of FIG. 9), making it possible to secure electrical conduction path 46 among mechanical probe 18, micro-sample 27 and sample table 28; thus, the contact detection becomes operating properly ((d) of FIG. 9).

FIG. 10 shows an embodiment of the conductive film formation to top and side surfaces plus bottom cut plane of a micro-sample in the case of the extracted micro-sample's bottom portion being fastened to sample table. Part (a) of FIG. 10 is a diagram schematically showing a state prior to causing the micro-sample 27 extracted by mechanical probe 18 to come into contact with the top face of sample table 28. While maintaining this state, deposition is applied to the top surface 43 and side surface 44 of micro-sample 27. The (b) of FIG. 10 shows a way of forming a conductive film while spouting gas 45 from deposition nozzle 19 and irradiating FIB 24. The (c) of FIG. 10 is a schematic diagram showing a state after having rotated micro-sample 27 to α-direction using a rotation mechanism of mechanical probe 18 after conductive film 23 was formed on top and side surfaces 43 and 44. Next, while keeping this state unchanged, deposition is applied to the bottom cut plane 51 of micro-sample 27. The (d) of FIG. 10 shows a way of forming a conductive film while spouting gas 45 from deposition nozzle 19 and irradiating FIB 24 in the sample state that the side face and bottom cut plane are viewable from FIB 24. By the processing stated above, conductive film 23 is also formed on bottom cut section 51 ((e) of FIG. 10). The rotation mechanism of mechanical probe 18 is used to return to the original angle ((f) of FIG. 19). It is possible to secure electrical conduction path 46 among mechanical probe 18, micro-sample 27 and sample table 28; thus, the contact detection becomes operating properly ((g) of FIG. 10).

FIG. 11 shows an embodiment of the conductive film formation to the top and side surfaces and bottom portion of a micro-sample in the case of the extracted micro-sample's side surface being fixed to sample table. Part (a) of FIG. 11 is a diagram schematically showing a state prior to causing the micro-sample 27 extracted by mechanical probe 18 to make contact with the top surface of sample table 28. Next, deposition is applied to top surface 43 and side surface 44. The (b) of FIG. 11 shows a way of forming a conductive film while spouting gas 45 from deposition nozzle 19 and irradiating by FIB 24. By this processing, conductive film 23 is formed on top and side surfaces 43, 44 ((c) of FIG. 11), and electrical conduction path 46 is secured among mechanical probe 18, micro-sample 27 and sample table 28; thus, the contact detection becomes operating properly ((d) of FIG. 11). Additionally, in the case of fastening the micro-sample's side surface to sample table, the following procedure may be employed. Firstly, as has been explained in FIG. 10, deposition is applied to the micro-sample's top and side surfaces, forming a conductive film. Next, the rotation mechanism of mechanical probe is used to rotate the micro-sample; then, deposition is applied to the bottom cut plane in the sample state that the bottom cut plane is viewable from FIB 24, thereby forming the conductive film. Fixation to the sample table may be performed without doing any extra processing; alternatively, it is done after having returned the rotation angle to its original state.

Figure 12A:
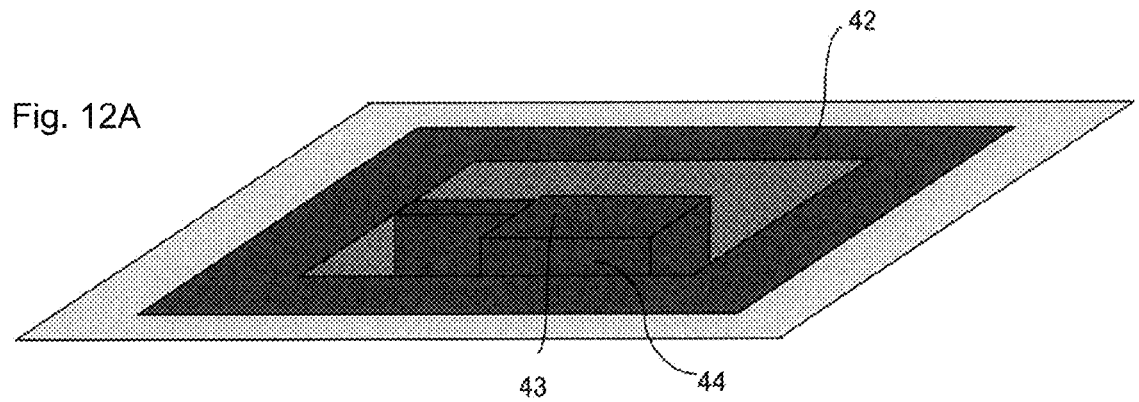
FIGS. 12A-12C are embodiments of conductive film formation to a sample surface in accordance with this invention.
Figure 12B:
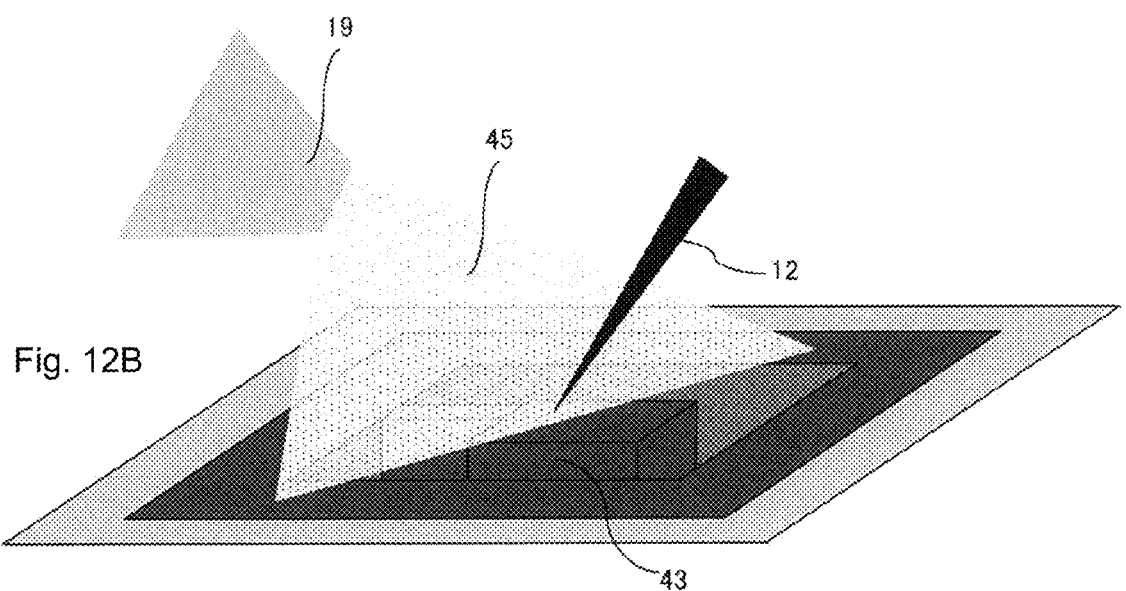
Figure 12C:
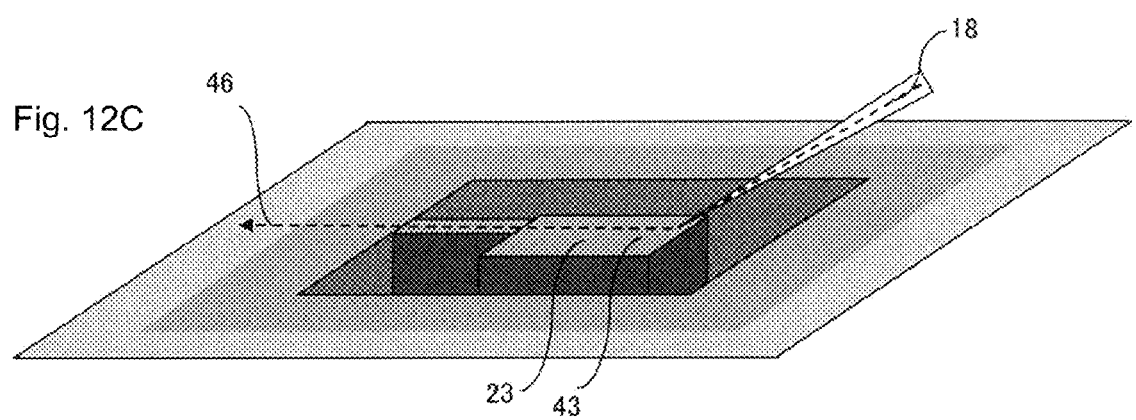
Figure 13A:
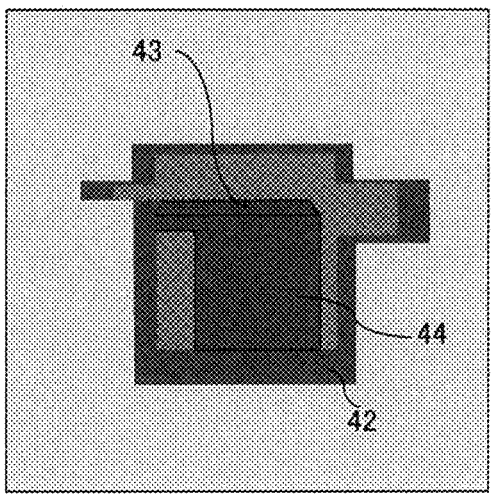
FIGS. 13A-13F are embodiments of conductive film formation to a sample surface in accordance with this invention.
Figure 13B:
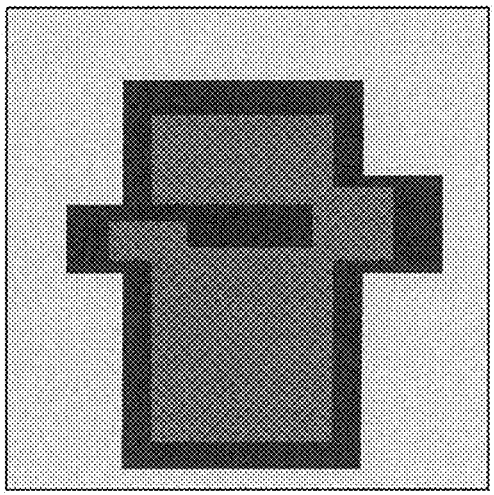
Figure 13C:
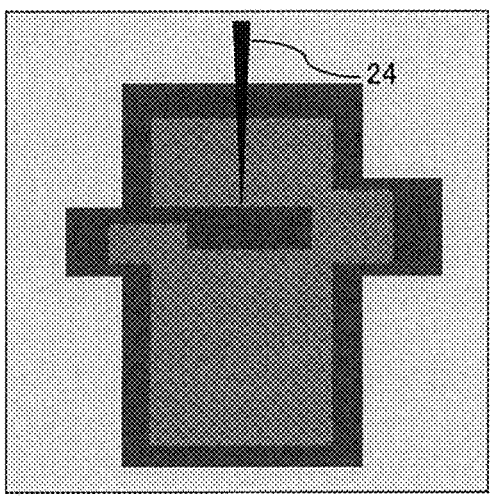
Figure 13D:
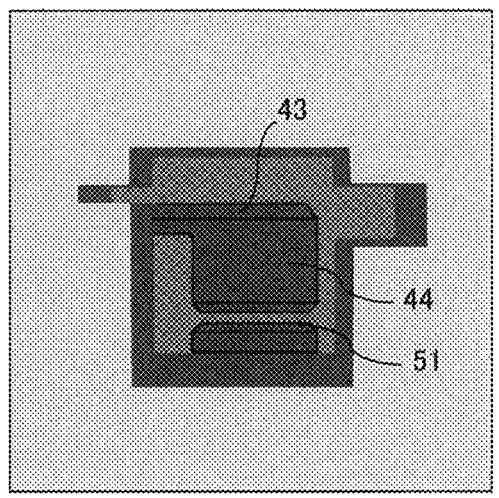
Figure 13E:
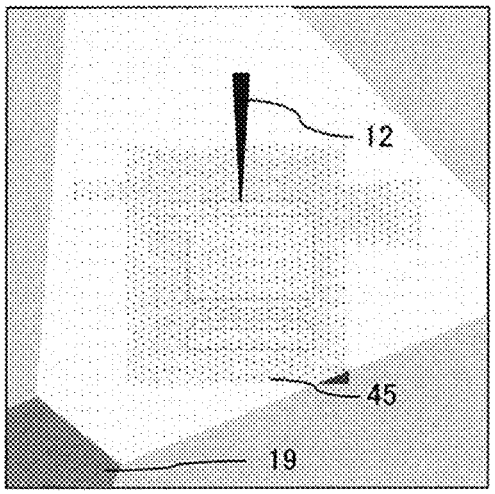
Figure 13F:
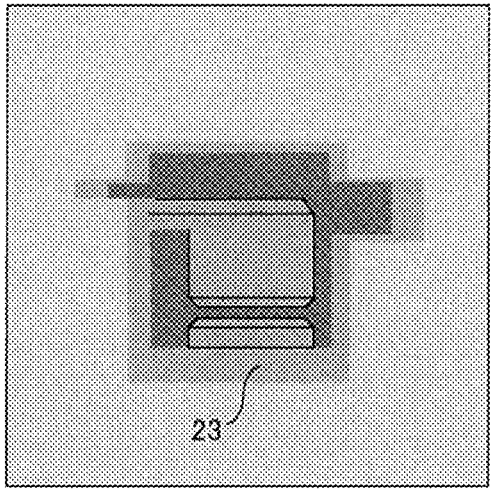

The embodiments of FIG. 5 to FIG. 11 are the embodiments relating to the FIB-based conductive film formation; so, these are implementable with the use of any one of FIB device, FIB-SEM device and FIB-STEM device. However, the electron beam-used conductive film formation is implementable by only the FIB-SEM and FIB-STEM devices. Namely, the embodiments of FIGS. 5 to 11 are such that similar processing becomes implementable even when using an electron beam in place of the FIB used for conductive film formation. Here, as a representative example, there will be shown an embodiment in the case of using the electron beam for the conductive film formation in relation to the embodiments of FIGS. 5 and 6. FIG. 12 is an embodiment of the conductive film formation to sample surface in accordance with this invention. After having performed peripheral processing and bottom cutting, sputter material 42 reattaches to top surface 43 and side surface 44 ((a) of FIG. 12). As the processed part is electrically isolated, electrical conduction between the mechanical probe and sample is no longer secured, posing the problem that contact detection becomes disabled. To avoid this, a conductive film is formed on the surface by using the deposition function ((b) of FIG. 12). Shown in (b) of FIG. 12 is a way of forming conductive film while spouting gas 45 from deposition nozzle 19 and scanning by FIB 24. With this processing, conductive film 23 is formed on surface 43, and electrical conduction path 46 is secured between mechanical probe 18 and surface 43; thus, the contact detection becomes operating properly ((c) of FIG. 12).

FIG. 13 is an embodiment of the conductive film formation to sample surface in accordance with this invention. The observation direction of each figure is set to the incoming direction of an electron beam. Similarly to FIG. 12, suppose that the peripheral processing-generated sputter material 42 reattached to top and side surfaces 43 and 44 ((a) of FIG. 13). The sample inclines ((b) of FIG. 13); its bottom portion is cut by FIB 24 ((c) of FIG. 13). In (c) of FIG. 3, depiction is eliminated as the bottom portion is not viewable from the electron beam's incoming direction. The sample inclination or tilt is set back ((d) of FIG. 13). While keeping this state, deposition is applied to top and side surfaces 43, 44 and bottom cut plane 51. The (e) of FIG. 13 shows a way of forming a conductive film while spouting gas 45 from deposition nozzle 19 and scanning by FIB 24. In order to apply deposition to the bottom cut plane more reliably, the deposition may be done after having performed angle adjustment so as to enable the bottom cut plane to be observable by electron beam. By this processing, conductive film 23 is formed, and electrical conduction path 46 is secured between the mechanical probe and sample surface; thus, the contact detection becomes operating properly ((f) of FIG. 13). Note here that (a), (d), (e) and (f) of FIG. 13 shrink the scale in the longitudinal direction because the observation is being performed in the state that the sample is tilted.

Figure 14A:
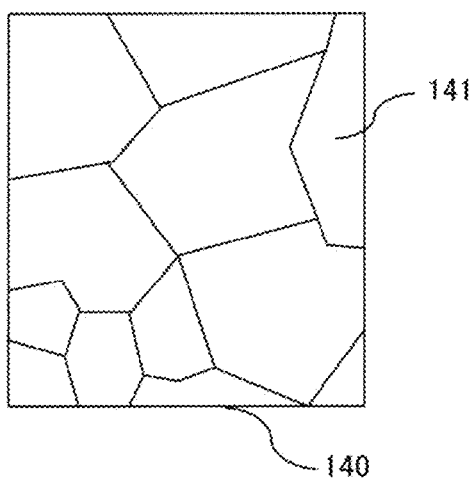
FIGS. 14A and 14B are schematic diagrams of a sample cross-section structure capable of applying this invention.
Figure 14B:
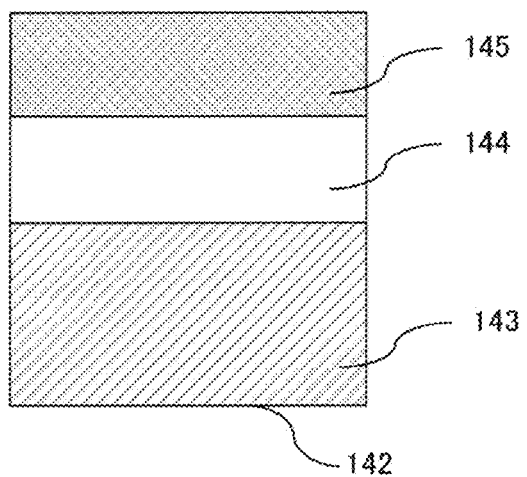

FIG. 14 shows pictorial representations of sample cross-sectional structures to which this invention can be applied. This invention is applicable to certain kinds of materials incapable of securing the electrical conduction path, such as samples partly containing a dielectric material in dielectric material or conductive material. The invention is also usable for materials with conductivity. Part (a) of FIG. 14 is a schematic cross-sectional diagram of dielectric material. Examples of the dielectric material are various kinds of materials, such as ceramics, polymer, bio samples, etc. Here, an example of ceramics is shown as one representative example. Typically, ceramics 140 has a sintered body structure of a great number of gains 141. The (b) of FIG. 14 is a schematic sectional diagram of a sample which partly contains dielectric material in conductive material. Here, as a representative example, an example of semiconductor is shown. For simplicity purposes, the semiconductor 142 is arranged to have a multilayer structure with a dielectric film 144 and conductive film 145 being laminated on or above Si substrate 143, which is conductive material. This is faced with a problem that electrical conduction path is not securable because dielectric film 144 exists between Si substrate 143 and conductive film 146 even when the mechanical probe makes contact with the surface of conductive film. By applying this invention thereto, it is possible to secure the electrical conduction path between the mechanical probe and original sample, thereby making the contact detection operable. In addition, applying this invention to extracted micro-samples makes it possible to acquire electrical conductivity among the mechanical probe, micro-sample and sample table, thus enabling successful achievement of the contact detection.

Figure 15:
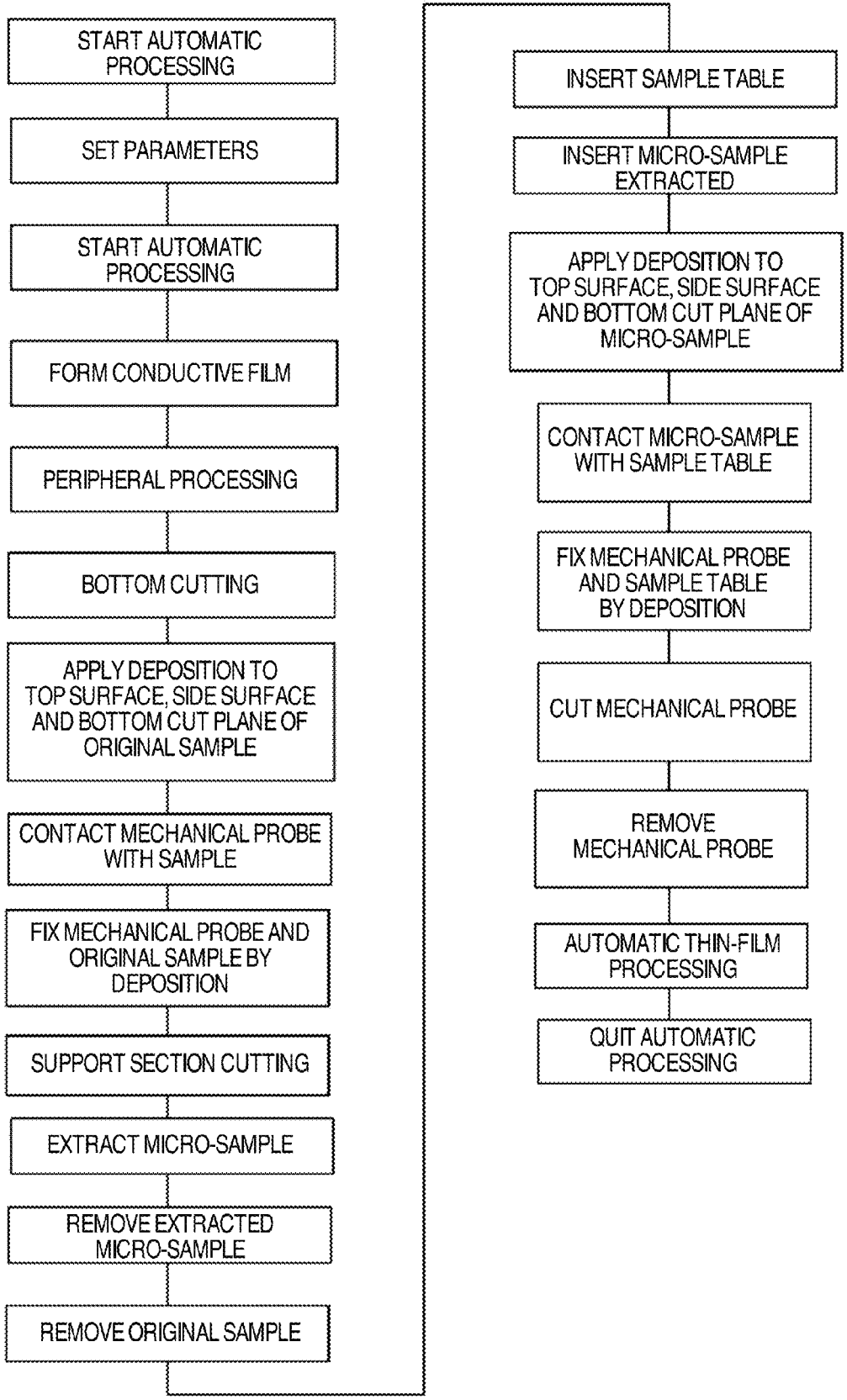
FIG. 15 is a procedure in the event of applying this invention to the automatic machining/fabrication of a microsampling method.

The embodiments of from FIG. 5 to FIG. 14 are applicable to manual manipulation and automated processing of microsampling method. FIG. 15 shows a fabrication/processing procedure in the event of applying this invention to the automated processing of microsampling method. First, prior to startup of the automatic processing, parameter setting is performed. The parameters include those indicating a processing area size, processing time, processing location, extracted sample fixation location and others. The automatic processing gets started. Deposition-based conductive film formation, peripheral processing and bottom cutting are performed. By using this invention, deposition is applied to its top and side surfaces and bottom cut plane, forming a conductive film. The mechanical probe is inserted. This mechanical probe is brought into contact with sample surface. Electrical conduction path is secured, making the contact detection operable. Its apical end and original sample are fastened by deposition. The supporting section is cut by FIB. A micro-sample is extracted and then removed together with the mechanical probe. The original sample is removed. The sample table is inserted. The micro-sample extracted is inserted. Using this invention, deposition is applied to the extracted micro-sample's top and side surfaces and bottom cut plane, forming a conductive film. The micro-sample is brought into contact with sample table. Electrical conduction path is secured, causing the contact detection to operate. The micro-sample and sample table are fixed by deposition. The mechanical probe is cut by FIB. The mechanical probe is driven to move out. Thereafter, automatic thin-film fabrication is performed, making a thin-film sample. Note here that in the case of aiming at SEM cross-section observation, it is permissible to perform only the FIB-used cross-section finishing. By applying this invention, it becomes possible to implement the procedure up to the thin-film sample preparation in an automated way. Additionally, the above-stated procedure is also achievable by manual manipulation of microsampling method.

Although this invention has been described with reference to particular embodiments, the description is not to be construed as limiting the invention, and various modifications and alterations may occur to those skilled in the art without departing from the spirit and scope of the invention as defined by the appended claims.

REFERENCE SIGNS LIST

1 Ion Beam Irradiation System
2 Ion System
3 Focusing Lens
4 Deflector
5 Objective Lens
6 Ion Beam
7 Electron Beam Irradiation System
8 Electron System
9 Focusing Lens
10 Deflector
11 Objective Lens
12 Electron Beam
13 Original Sample
14 Sample Stage
15 Chamber
16 Secondary Charged Particle
17 Secondary Charged Particle Detector
18 Mechanical Probe
19 Deposition Nozzle
20 Pump
21 Control Unit
22 CRT
23 Conductive Film
24 FIB
25 Bottom Portion
26 Supporting Section
27 Micro-sample
28 Sample Table
29 Thin-film Sample
31 Contact Detection Judging Unit
41 Conductive Material
42 Sputter Material
43 Top Surface
44 Side Surface
45 Gas
46 Electrical Conduction Path
51 Bottom Cut Plane
140 Ceramics
141 Grains
142 Semiconductor
143 Si Substrate
144 Dielectric Film
145 Conductive Film

The invention claimed is:

1. A charged particle beam device comprising:
a charged particle source;
an objective lens configured to focus a charged particle beam emitted from said charged particle source onto a sample;
a detector configured to detect secondary charged particles to be emitted from said sample;
a probe capable of coming into contact with said sample;
a gas nozzle configured to emit a conductive gas to said sample; and
a control unit configured to control driving of said probe and gas emission from said gas nozzle,
wherein said control unit has a contact detection unit,
wherein after having applied processing by irradiating the charged particle beam to said sample so as to separate a part of said sample as a micro-sample, a conductive film is formed on said micro-sample by emitting the gas from said gas nozzle toward said micro-sample and simultaneously irradiating said charged particle beam prior to fastening one surface of the micro-sample processed by said probe on a sample table, and
wherein said contact detection unit detects electrical conduction between said micro-sample and said sample table.

2. The charged particle beam device according to claim 1, wherein after having applied the processing for separating a part of said sample as the micro-sample by irradiating said charged particle beam to said sample, said control unit fastens said probe and the processed micro-sample, extracts said micro-sample from said sample and fastens one surface of the extracted micro-sample onto the sample table.

3. The charged particle beam device according to claim 2, comprising a rotation mechanism capable of rotating said probe, and wherein said control unit forms a conductive film on said micro-sample by emitting the from said gas nozzle toward said micro-sample and simultaneously irradiating said charged particle beam in a state of fastening said probe and said micro-sample before and after a rotation operation of said probe performed by said rotation mechanism, and
wherein said contact detection unit detects electrical conduction between said micro-sample and said sample table.

4. A charged particle beam device comprising:
an ion source;
an objective lens configured to focus an ion beam emitted from said ion source onto a sample;
an electron source;
an objective lens configured to focus an electron beam emitted from said electron source onto the sample;
a detector configured to detect secondary charged particles to be emitted from said sample;
a probe capable of coming into contact with said sample;
a gas nozzle configured to emit a conductive gas to said sample; and
a control unit configured to control driving of said probe and gas emission from said gas nozzle,
wherein said control unit has a contact detection unit,
wherein after having applied processing by irradiating the ion beam to said sample so as to separate a part of said sample as a micro-sample, a conductive film is formed on said micro-sample by emitting the gas from said gas nozzle toward said micro-sample and simultaneously irradiating said electron beam prior to fastening one surface of the micro-sample processed by said probe on a sample table, and
wherein said contact detection unit detects electrical conduction between said micro-sample and said sample table.

5. The charged particle beam device according to claim 4, wherein after having applied the processing for separating a part of said sample as the micro-sample by irradiating said charged particle beam to said sample, said control unit controls said probe so as to fasten said probe and the processed micro-sample, extract said micro-sample from said sample, and fasten one surface of the extracted micro-sample onto the sample table.

6. The charged particle beam device according to claim 5, comprising a rotation mechanism capable of rotating said probe,
wherein said control unit forms a conductive film on said micro-sample by emitting the gas from said gas nozzle toward said micro-sample and simultaneously irradiating said charged particle beam in a state of fastening said probe and said micro-sample before and after a rotation operation of said probe performed by said rotation mechanism, and
wherein said contact detection unit detects electrical conduction between said micro-sample and said sample table.

7. A micro-sample processing observation method using a charged particle beam device having:
a charged particle source,
an objective lens configured to focus a charged particle beam emitted from said charged particle source onto a sample,
a detector configured to detect secondary charged particle to be emitted from said sample, a probe capable of coming into contact with said sample,
a gas nozzle configured to emit a conductive gas to said sample, and
a control unit configured to control driving of said probe and gas emission from said gas nozzle,
wherein said control unit has a contact detection unit,
wherein after having applied processing by irradiating the charged particle beam to said sample so as to separate a part of said sample as a micro-sample, a conductive film is formed on said micro-sample by emitting the gas from said gas nozzle toward said micro-sample and simultaneously irradiating said charged particle beam prior to fastening one surface of the micro-sample processed by said probe on a sample table, and
wherein said contact detection unit detects electrical conduction between said micro-sample and said sample table.

8. The micro-sample processing observation method according to claim 7, wherein said control unit forms a conductive film on said micro-sample by emitting the gas from said gas nozzle toward said micro-sample and simultaneously irradiating said charged particle beam in a state of fastening said probe and said micro-sample before and after a rotation operation of said probe performed by said rotation mechanism, and
wherein said contact detection unit detects electrical conduction between said micro-sample and said sample table.

* * * * *